United States Patent
Hyun

(10) Patent No.: US 8,272,131 B2
(45) Date of Patent: *Sep. 25, 2012

(54) METHOD OF MANUFACTURING A FIXTURE OF DENTAL IMPLANT

(76) Inventor: Young Keun Hyun, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 13/113,172

(22) Filed: May 23, 2011

(65) Prior Publication Data

US 2011/0223561 A1    Sep. 15, 2011

Related U.S. Application Data

(63) Continuation of application No. PCT/KR2009/006907, filed on Nov. 24, 2009.

(30) Foreign Application Priority Data

Nov. 25, 2008   (KR) .................. 10-2008-0117323

(51) Int. Cl.
*A61C 5/09*   (2006.01)
*A61C 8/00*   (2006.01)

(52) U.S. Cl. ..................... 29/896.1; 433/174
(58) Field of Classification Search .......... 29/896.1; 433/174, 173, 192, 201.1, 207, 219–221, 433/223

See application file for complete search history.

(56) References Cited

U.S. PATENT DOCUMENTS

| | | | |
|---|---|---|---|
| 5,078,607 A | 1/1992 | Niznick | |
| 5,316,476 A | 5/1994 | Krauser | |
| 5,324,199 A | 6/1994 | Branemark | |
| 5,478,237 A * | 12/1995 | Ishizawa | 433/201.1 |
| 5,947,735 A * | 9/1999 | Day | 433/173 |
| 6,220,861 B1 | 4/2001 | Kwon et al. | |
| 6,626,671 B2 * | 9/2003 | Klardie et al. | 433/201.1 |
| 2003/0158554 A1 * | 8/2003 | Hall | 606/72 |
| 2007/0172796 A1 | 7/2007 | Hyun et al. | |

FOREIGN PATENT DOCUMENTS

| | | |
|---|---|---|
| KR | 10-0283988 B1 | 2/2000 |
| KR | 20000006624 A | 2/2000 |
| KR | 10-0718278 B1 | 5/2007 |

OTHER PUBLICATIONS

International Search Report; mailed Jul. 15, 2010; Appln. PCT/KR2009/006907.

* cited by examiner

*Primary Examiner* — Sarang Afzali
(74) *Attorney, Agent, or Firm* — Ladas & Parry LLP

(57) ABSTRACT

Provided are a fixture of a dental implant and a method of manufacturing the same, and more particularly, a method of manufacturing a fixture of a dental implant easily that allows fast bone formation at an early stage and prevents infection and inflammation, and a fixture of a dental implant having an improved structure that can be manufactured by using the method of manufacturing the same. The fixture of a dental implant with an improved structure in which the performance of osseointegration is excellent and spread of inflammation is reduced, and the method of manufacturing the fixture of a dental implant easily are provided. In the method of manufacturing a fixture of a dental implant, the fixture of the dental implant in which the performance of osseointegration is excellent and spread of inflammation can be reduced, can be easily manufactured. Furthermore, in the fixture of the dental implant, the performance of osseointegration is excellent and spread of inflammation can be reduced.

7 Claims, 10 Drawing Sheets

US 8,272,131 B2

METHOD OF MANUFACTURING A FIXTURE OF DENTAL IMPLANT

CROSS-REFERENCE TO RELATED PATENT APPLICATION

This application claims the benefit of Korean Patent Application No. 10-2008-0117323, filed on Nov. 25, 2008, in the Korean Intellectual Property Office, the disclosure of which is incorporated herein in its entirety by reference.

BACKGROUND OF THE INVENTION

1. Field of the Invention

The present invention relates to a fixture of a dental implant and a method of manufacturing the same, and more particularly, to a method of manufacturing a fixture of a dental implant easily that allows fast bone formation at an early stage and prevents infection and inflammation, and a fixture of a dental implant having an improved structure that can be manufactured by using the method of manufacturing the same.

2. Description of the Related Art

Generally, dental implants include a fixture, an abutment, and a crown.

A male screw portion is formed in the fixture, is inserted in an alveolar bone of a human body and supports and fixes a dental implant.

The abutment is combined with an upper portion of the fixture and is exposed to an upper portion of gingiva.

The crown is one kind of prosthesis that replaces natural tooth, is engaged with the abutment and is adhered and fixed to the abutment.

In order to achieve the success of implants, osseointegration between the fixture and the alveolar bone has to be successfully performed. When osseointegration is not successfully done, bone resorption or progressive bone loss occurs.

It is widely known that a surface roughness of the fixture affects the success of osseointegration. When the surface of the fixture becomes rough by increasing the surface roughness of the fixture, a contact surface between the implant and a surrounding bone is increased, and cell adsorption is improved, so that positive effects can be obtained.

However, the rough surface of the fixture promotes progress of infection when inflammation occurs around the implant. In other words, it is reported that, when the surface of the fixture is rougher than a polished surface, infection progresses more quickly along the surface of the fixture.

In order to solve the problem, as illustrated in FIG. 1, Korean Patent Application No. 283988 and Korean Patent Application No. 718278 disclose an 'osseointegration artificial tooth' in which the surface of a fixture 1 is overall rough and a polished band 3 having a low surface roughness is formed in a waist portion of a screw portion 2 of the fixture 1 so as to improve the performance of osseointegration and prevent progress of inflammation around a dental implant due to the polished band 3.

A method of manufacturing a dental implant or a fixture of a dental implant having the above structure with high productivity easily is necessary, and the fixture of a dental implant having an improved structure so as to use the method is also necessary.

SUMMARY OF THE INVENTION

The present invention provides a fixture of a dental implant with an improved structure in which the performance of osseointegration is excellent and spread of inflammation is reduced, and a method of manufacturing the fixture of a dental implant easily.

According to an aspect of the present invention, a method of manufacturing a fixture of a dental implant includes: cutting the fixture of the dental implant to form a male screw portion of the fixture; performing jig fixing in such a way that a protection jig is inserted in the ring-shaped male screw portion to surround portions of the male screw portion of the fixture in a circumferential direction of the protection jig; performing surface processing on the male screw portion of the fixture to increase a surface roughness; and performing jig removal in such a way that the protection jig fixed on the male screw portion is removed from the male screw portion of the fixture.

According to another aspect of the present invention, a fixture of a dental implant fixed on an alveolar bone by using a male screw portion includes: a polished portion formed along an outer diameter of the male screw portion so as to have a low surface roughness; and an unpolished portion formed at the remaining portions of the male screw portion excluding the polished portion so as to have a surface that is more rough than a surface of the polished portion.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

FIGS. 2 through 5 illustrate a method of manufacturing a fixture 100 of a dental implant, according to an embodiment of the present invention.

Figure 1:
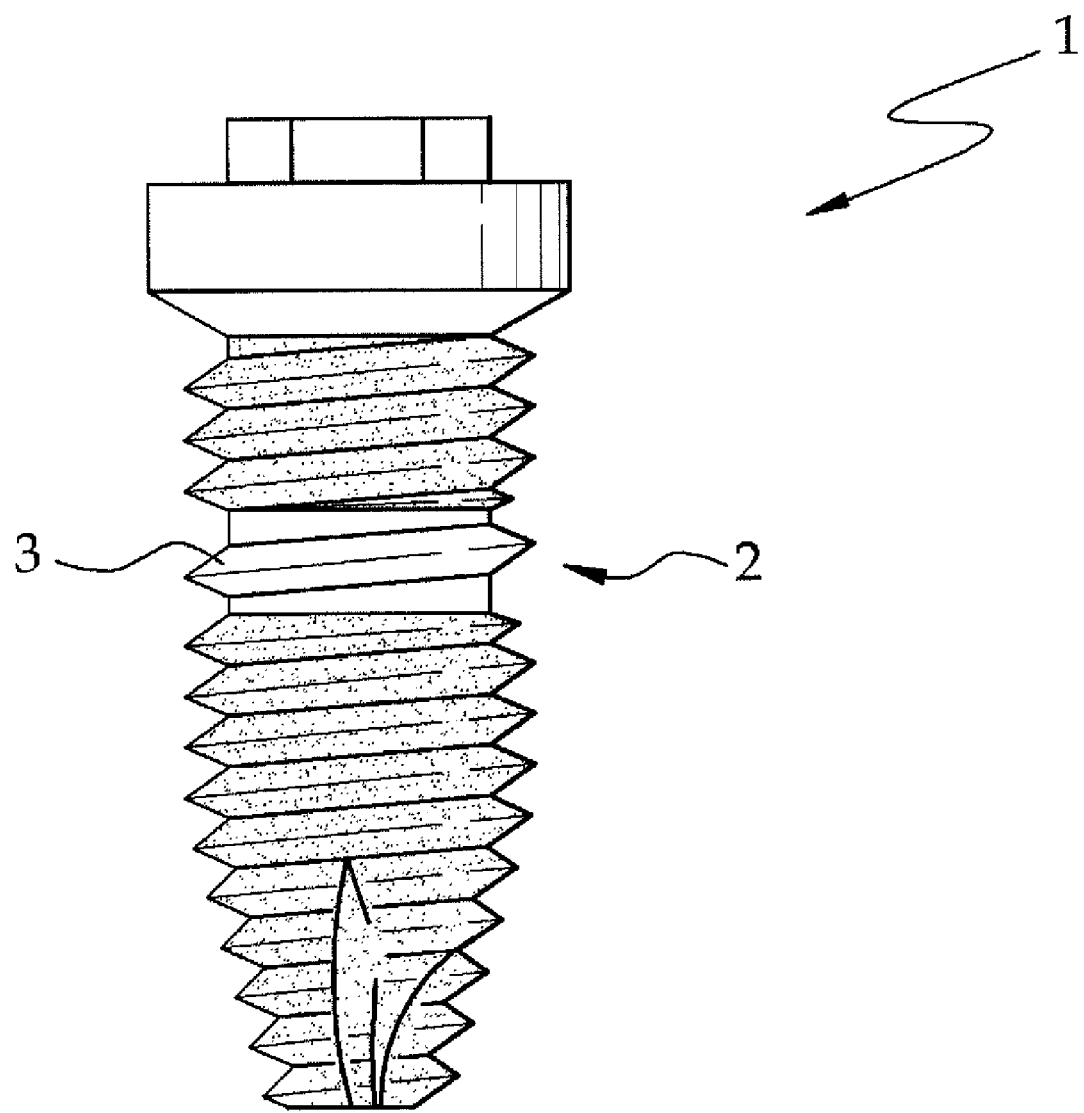
FIG. 1 illustrates a structure of a fixture of a dental implant according to the related art.
Figure 2:
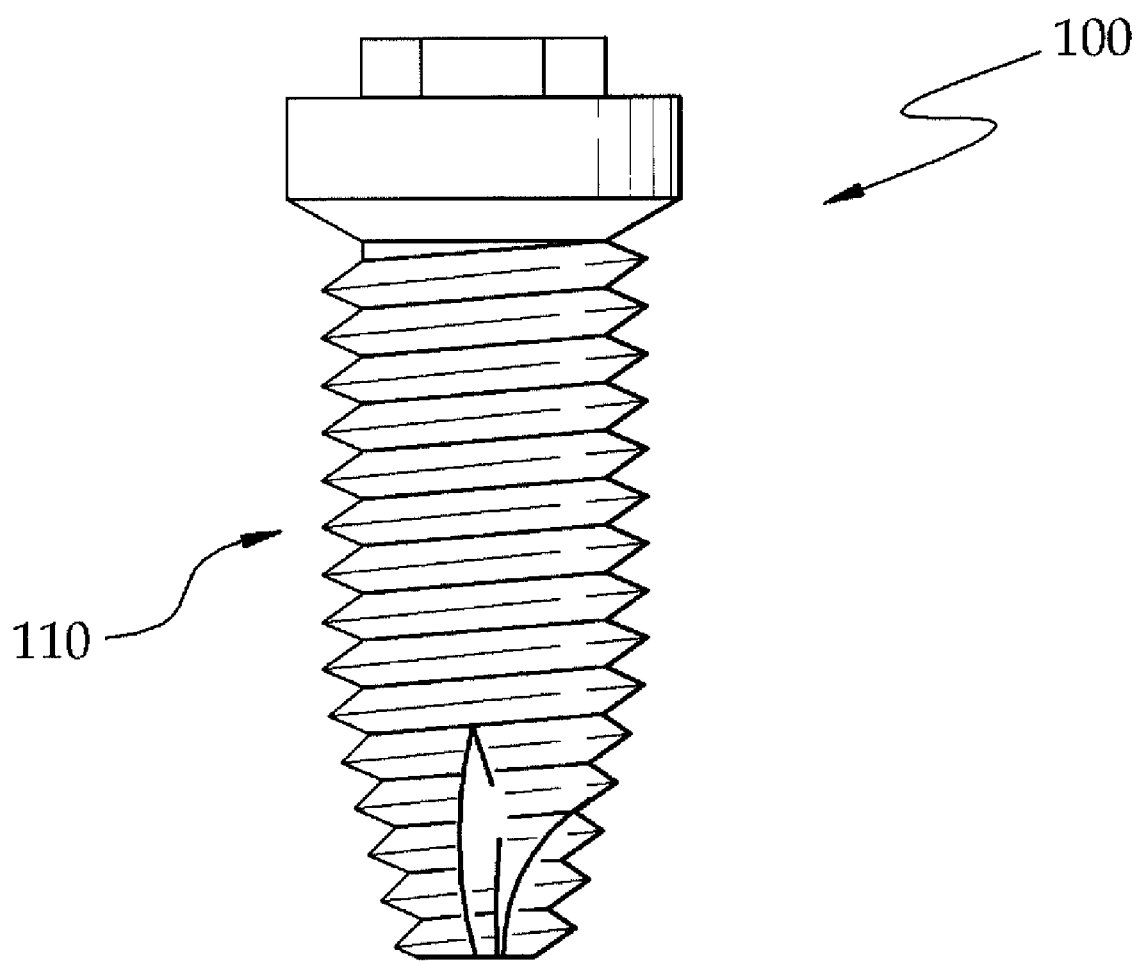
FIGS. 2 through 5 illustrate a method of manufacturing a fixture of a dental implant, according to an embodiment of the present invention.

Referring to FIG. 2, the method of manufacturing the fixture 100 of the dental implant according to the current embodiment of the present invention includes cutting the fixture 100 of the dental implant to form a male screw portion 110. A polished surface having a low surface roughness to a level of a machined surface is formed by a cutting tool of machine tools at the entire surface of the male screw portion 110. In this regard, the male screw portion 110 has an overall surface roughness in the range of 0.1 to 0.5 μm.

Figure 3:
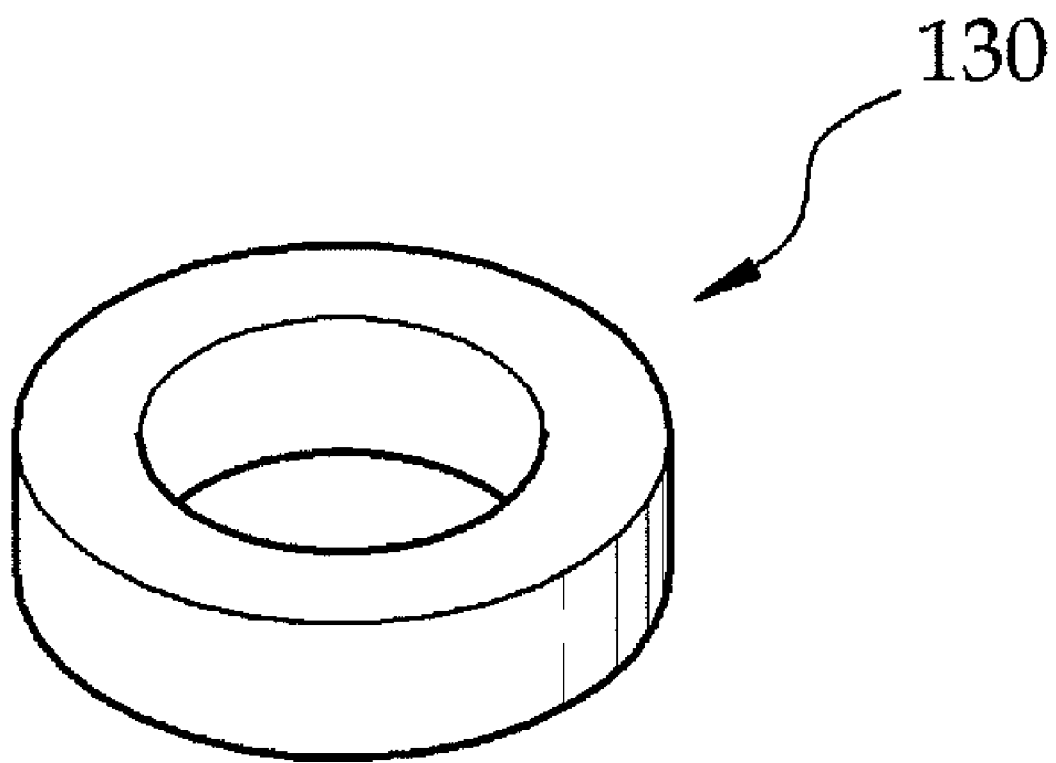

Separately, a protection jig 130 illustrated in FIG. 3 is provided. The protection jig 130 is ring-shaped and may be formed of polymer having elasticity.

Figure 4:
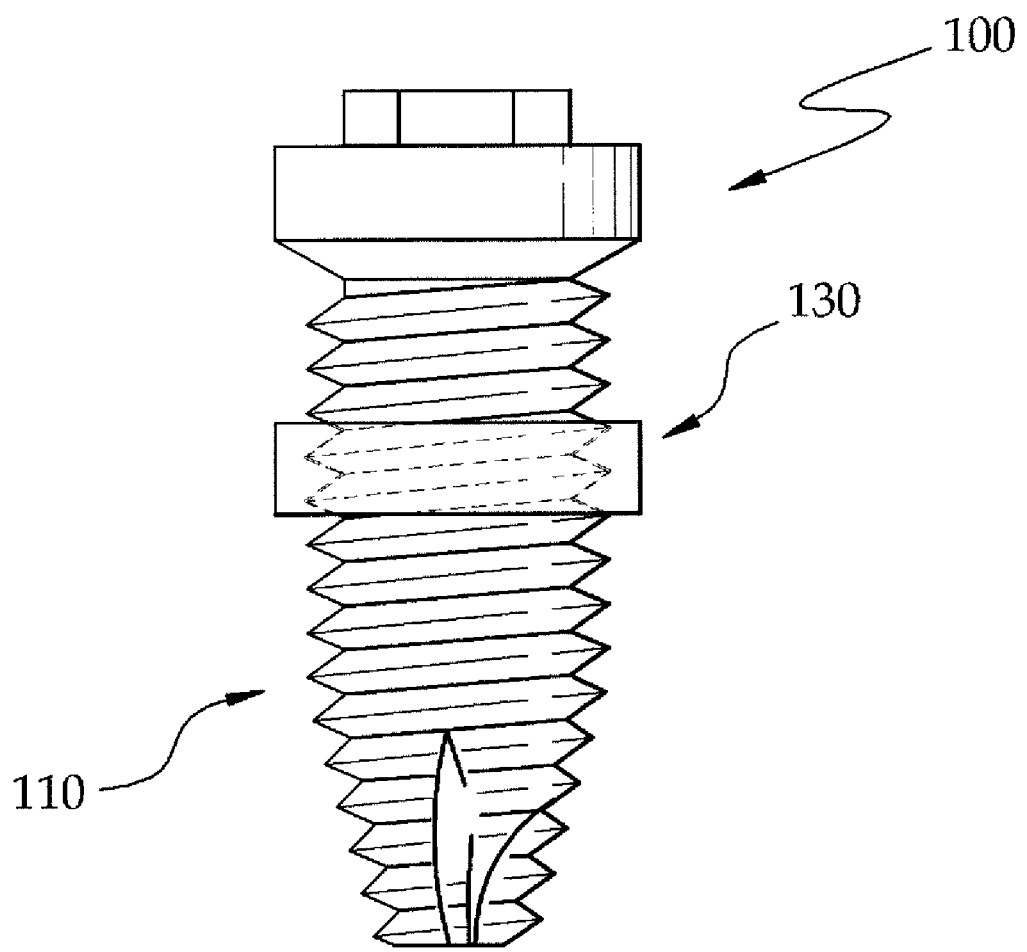

Jig fixing is performed in such a way that the protection jig 130 is inserted in the male screw portion 110 to surround portions of the male screw portion 110 of the fixture 100 in a circumferential direction of the protection jig 130, as illustrated in FIG. 4.

When the protection jig 130 is pushed into the male screw portion 110 of the fixture 100, the protection jig 130 is elastically deformed to securely surround an outer diameter of the male screw portion 110 of the fixture 100. In some cases, a female screw portion may be formed at an inside of the protection jig 130 so as to be screw-combined with the male screw portion 110 of the fixture 100 so that the male screw portion 110 of the fixture 100 and the female screw portion may be fixed to each other.

In this state, surface processing is performed in such a way that surface processing is performed on the male screw portion 110 of the fixture 100 so as to improve surface roughness. In other words, surfaces of the remaining portions excluding portions surrounded by the protection jig 130, of the male screw portion 110 of the fixture 100 are made rough. Surface processing may be performed by a method, such as sandblasting, anodization, etching, or the like. Such surface processing is performed so that the surface roughness of the male screw portion 110 is between 1.2 and 2.0 µm.

In this state, jig removal is performed in such a way that the protection jig 130 fixed on the male screw portion 110 is removed from the male screw portion 110 of the fixture 100.

Figure 5:
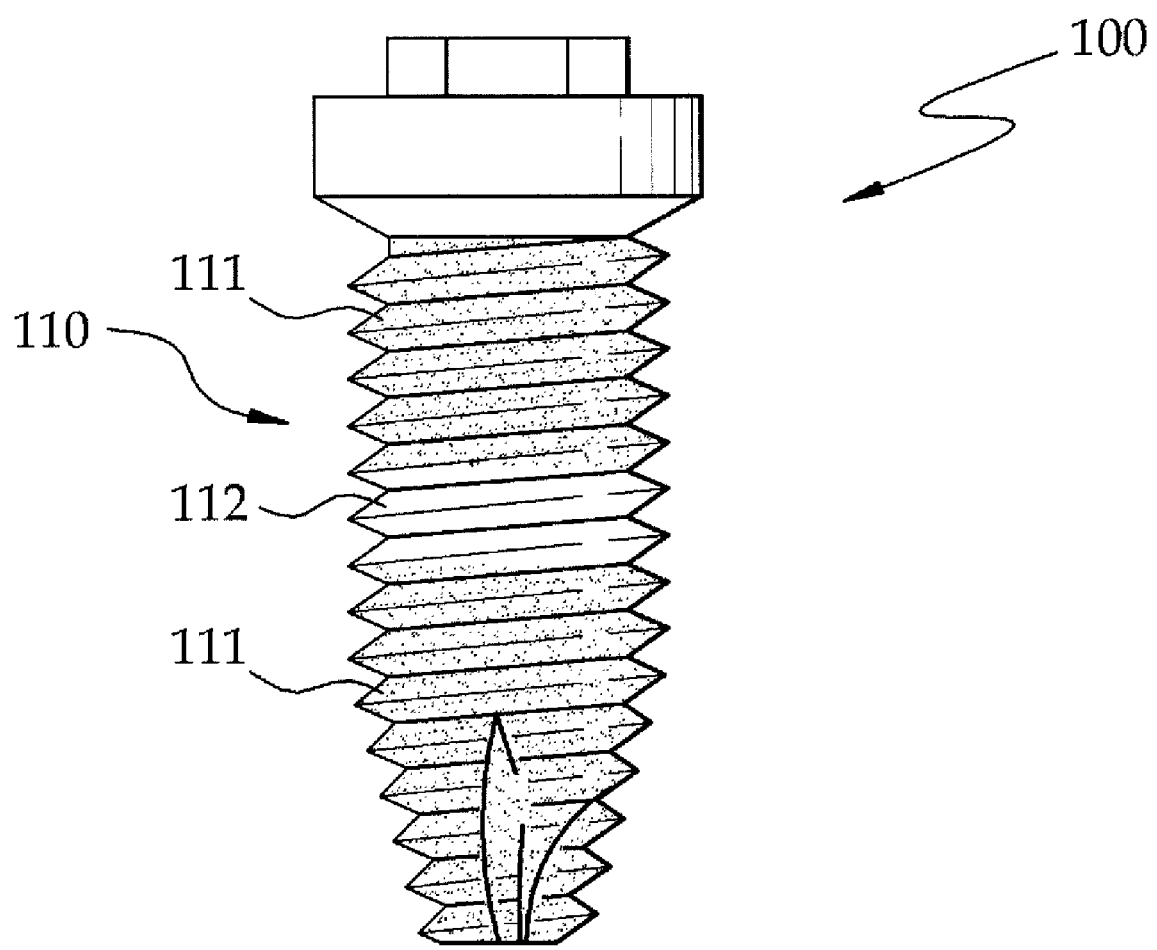

Referring to FIG. 5, portions of the male screw portion 110 in which the protection jig 130 is inserted, are not surface-processed but are maintained in the state of a low surface roughness and become a polished portion 112. The remaining portions of the male screw portion 110 excluding the polished portion 112 are surface-processed and become an unpolished portion 111 having a surface that is rougher than the surface of the polished portion 112.

In the fixture 100 of the dental implant manufactured by the method, a degree of osseointegration is improved due to the unpolished portion 111 having a high surface roughness, and inflammation may be prevented from being spread due to the polished portion 112 having a low surface roughness. Also, in the method of manufacturing the fixture 100 of the dental implant described above, the polished portion 112 may be easily formed at the fixture 100 of the dental implant having the above effects so that productivity of the fixture 100 may be improved.

Next, a method of manufacturing a fixture 200 of a dental implant, according to another embodiment of the present invention will be described.

FIGS. 6 through 9 illustrate a method of manufacturing the fixture 200 of a dental implant, according to another embodiment of the present invention.

Figure 6:
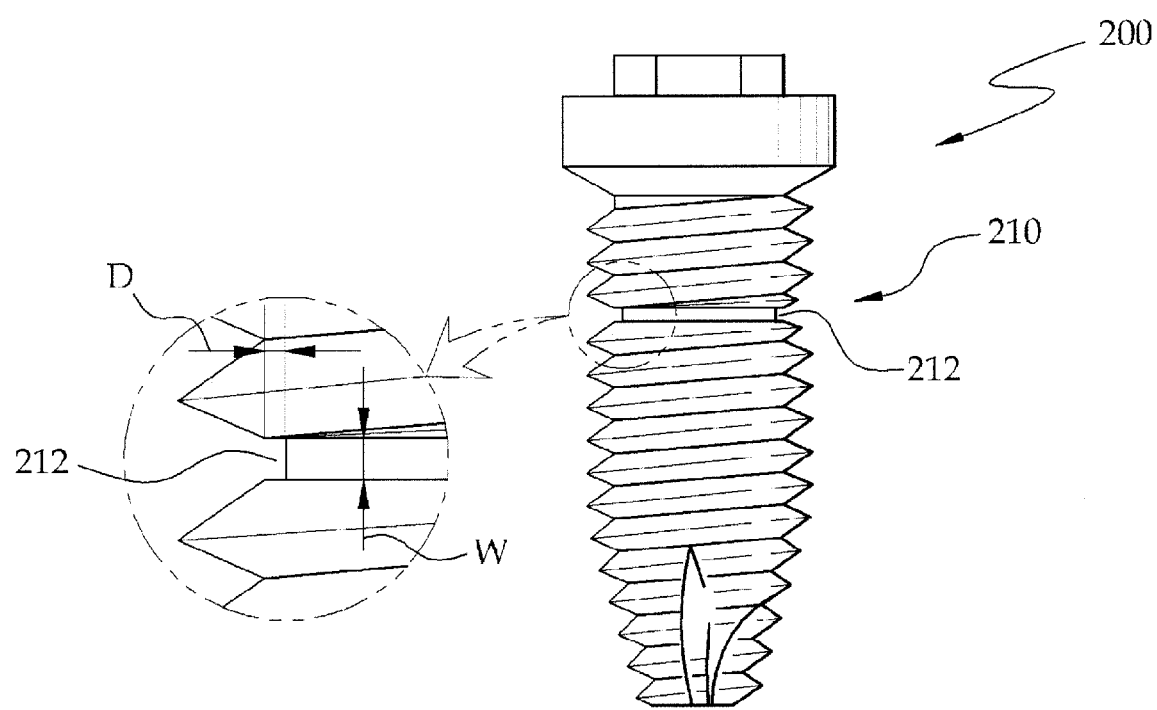
FIGS. 6 through 9 illustrate a method of manufacturing a fixture of a dental implant, according to another embodiment of the present invention.

Referring to FIG. 6, the method of manufacturing the fixture 200 of the dental implant according to the current embodiment of the present invention includes cutting the fixture 200 of the dental implant to form a male screw portion 210.

Next, as illustrated in FIG. 6, forming of a fixed groove 212 is performed in such a way that the fixed groove 212 is formed in the male screw portion 210 of the fixture 200 to surround portions of the male screw portion 210 in a circumferential direction of the male screw portion 210.

By performing the cutting of the fixture 200 and the forming of the fixed groove 212, the male screw portion 210 of the fixture 200 has a surface roughness in the range of 0.1 to 0.5 µm.

Figure 7:
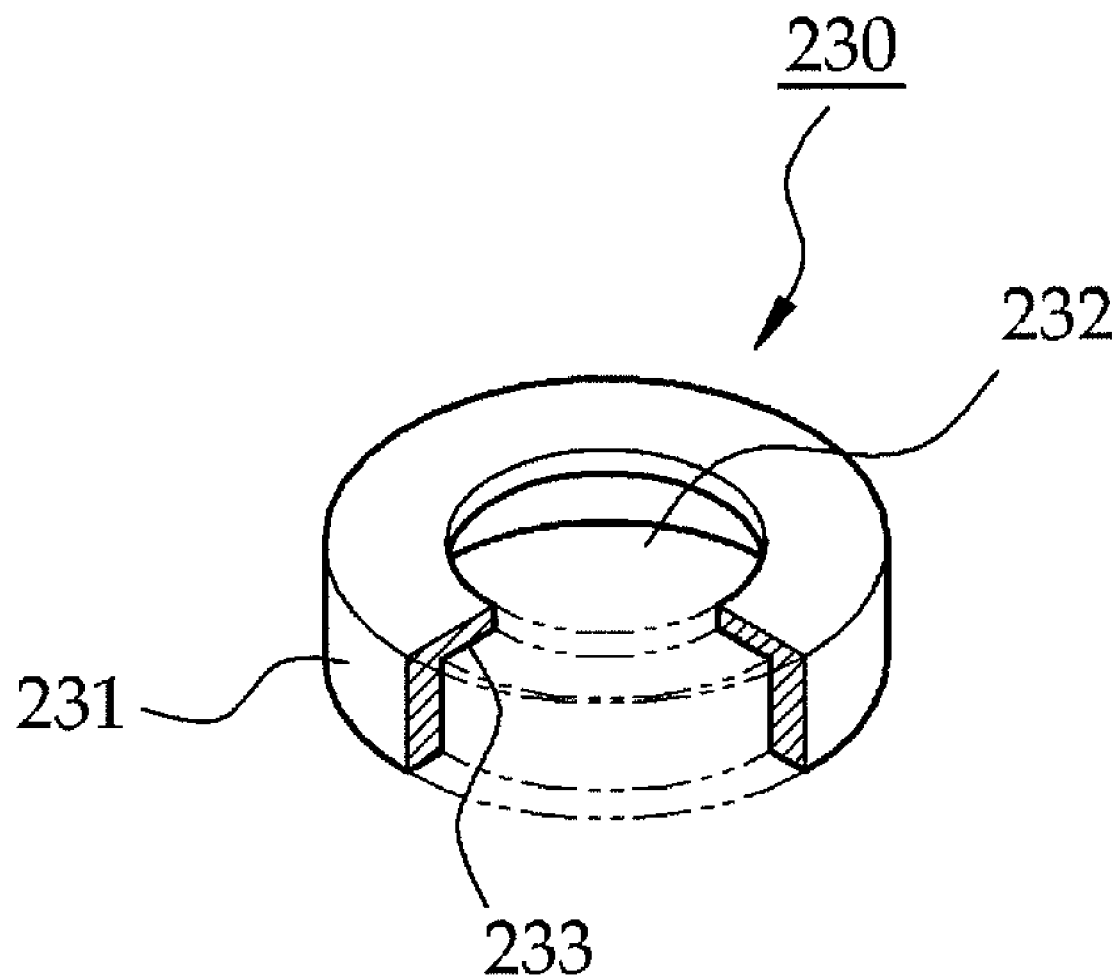

Separately, a protection jig 230 is provided, as illustrated in FIG. 7. The protection jig 230 includes a body portion and fixed protrusions 233. A combination hole 232 is formed in the body portion 231, and an inner diameter of the combination hole 232 is equal to or slightly smaller than an outer diameter of the male screw portion 210. The fixed protrusions 233 are formed in internal sides of the combination hole 232 so as to be inserted in the fixed groove 212 of the fixture 200 and fixed therein. The fixed protrusions 233 are ring-shaped, and may be formed of polymer having elasticity.

Figure 8:
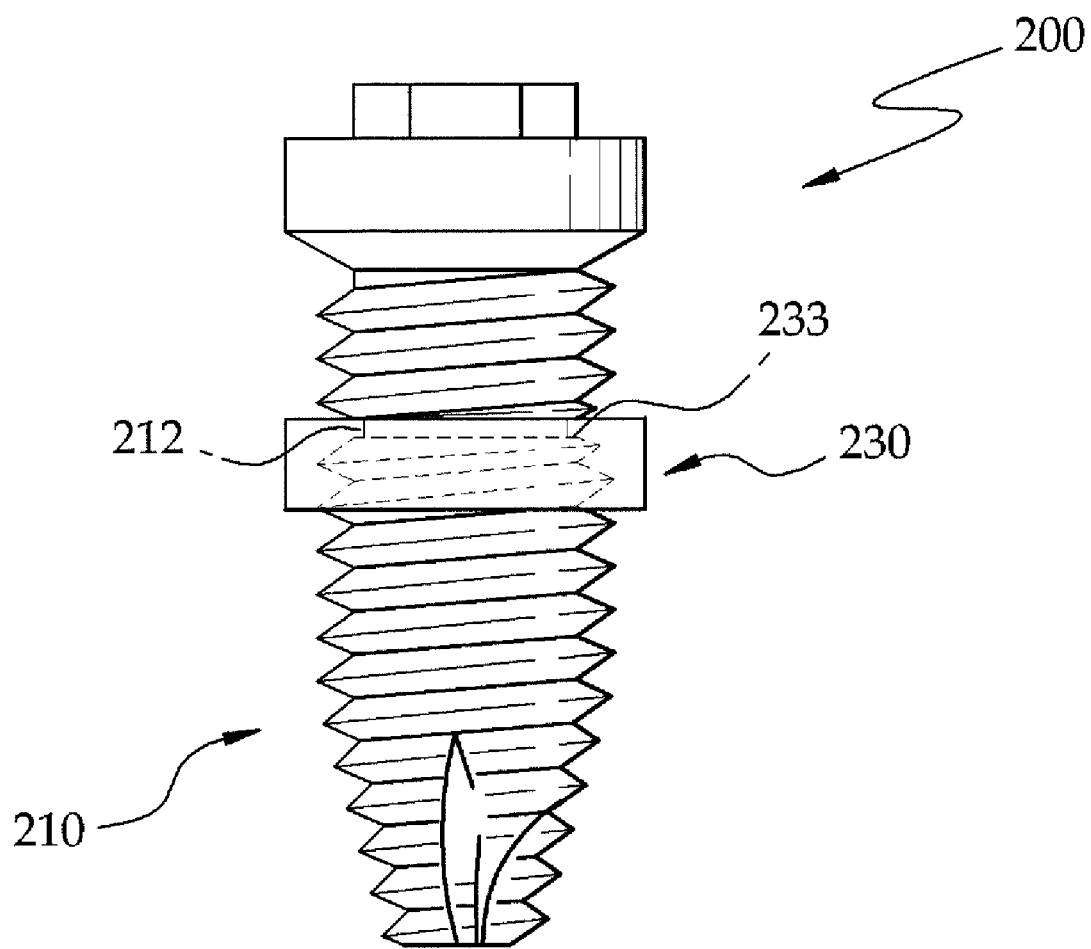

Jig fixing is performed in such a way that the protection jig 230 is inserted in the male screw portion 210 of the fixture 200 to surround portions of the male screw portion 210 in the circumferential direction of the protection jig 230, as illustrated in FIG. 8. In this regard, the fixed protrusions 233 of the protection jig 230 are inserted in the fixed groove 212 of the fixture 200 so that the protection jig 230 may not be shaken with respect to the fixture 200 and may be securely fixed on the fixture 200.

In this state, surface processing is performed in such a way that surface processing is performed on the male screw portion 210 of the fixture 200 so as to improve a surface roughness. In detail, surfaces of the remaining portions of the male screw portion 210 of the fixture 200 excluding portions surrounded by the protection jig 230 are made rough. Such surface processing may be performed by a method, such as sandblasting, anodization, etching, or the like.

When surface processing is performed using sandblasting, the surfaces of the remaining portions of the male screw portion 210 of the fixture 200 excluding the portions surrounded by the protection jig 230 are made rough by ejecting an abrasive into the male screw portion 210 at high speed. When the abrasive ejected into the male screw portion 210 at high speed collides with the protection jig 230, the protection jig 230 may be shaken with respect to the male screw portion 210 and may be escaped therefrom during the procedure. Since the fixture 200 of the dental implant that is recently used mostly has a tapered male screw portion 210 and an outer diameter of the fixture 200 is downwardly reduced, a possibility in which the protection jig 230 may be escaped from the male screw portion 210 is further increased.

However, as illustrated in FIG. 8, when the fixed protrusions 233 of the protection jig 230 and the fixed groove 212 of the fixture 200 are engaged with each other, the protection jig 230 is prevented from being escaped from the male screw portion 210 so that a defect rate may be reduced, productivity may be improved and quality of the fixture 200 may be improved.

Next, jig removal is performed in such a way that the protection jig 230 fixed on the male screw portion 210 is removed from the male screw portion 210 of the fixture 200.

Figure 9:
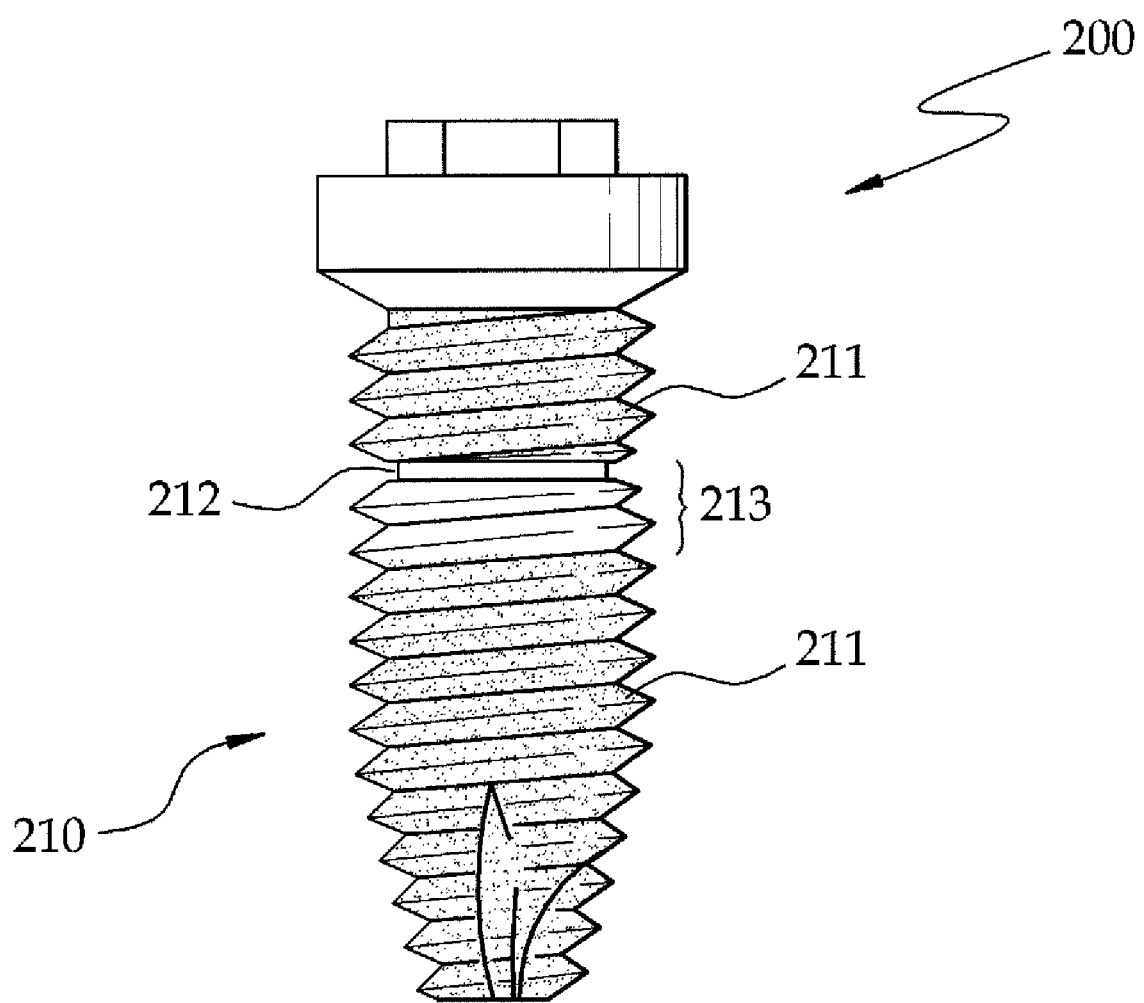

Referring to FIG. 9, portions of the male screw portion 210 in which the protection jig 230 is inserted, are not surface-processed but are maintained in the state of a low surface roughness and become a polished portion 213, and the remaining portions of the male screw portion 210 excluding the polished portion 213 become an unpolished portion 211 having a rough surface. The surface roughness of the unpolished portion 211 may be between 1.2 to 2.0 µm.

Referring to FIG. 6, a width W of the fixed groove 212 may be between 0.1 and 0.5 mm. When the width W of the fixed groove 212 is less than 0.1 mm, the fixed protrusions 233 of the protection jig 230 may not be well inserted in the fixed groove 212, and when the width W of the fixed groove 212 is greater than 0.5 mm, portions of the male screw portion 210 in which no threads are formed, become so large and a combination force between the fixture 200 and the alveolar bone may be reduced.

Also, a depth D of the fixed groove 212 with respect to screw valleys of the male screw portion 210 may be between 0.05 and 0.15 mm. When the depth D of the fixed groove 212 is less than 0.05 mm, the fixed protrusions 233 of the protection jig 230 may not be well inserted in the fixed grove 212, and when the depth D of the fixed groove 212 is greater than 0.15 mm, rigidity of the fixture 200 may be reduced.

Also, the polished portion 213 may be disposed in the range of 2 to 8 mm downwardly from an upper end of the male screw portion 210. When the polished portion 213 is located in the range of 2 mm from the upper end of the male screw portion 210, performance of preventing inflammation from being spread may be lowered, and when the polished portion 213 is located in the range of below 8 mm from the upper end of the male screw portion 210, the combination force between the fixture 200 and the alveolar bone may be reduced.

In the fixture 200 of the dental implant manufactured by the method of FIGS. 6 through 9, a degree of osseointegration is improved due to the unpolished portion 211 having a high surface roughness, and inflammation is prevented from being spread due to the polished portion 213 having a low surface roughness. Also, in the method of manufacturing the fixture 200 of the dental implant having the above-described structure, the polished portion 211 may be easily formed in the fixture 200 of the dental implant having the above effects so that productivity of the fixture 200 may be improved.

As described above, exemplary embodiments of the present invention have been described. However, aspects of the present invention are not limited thereto.

Figure 10:
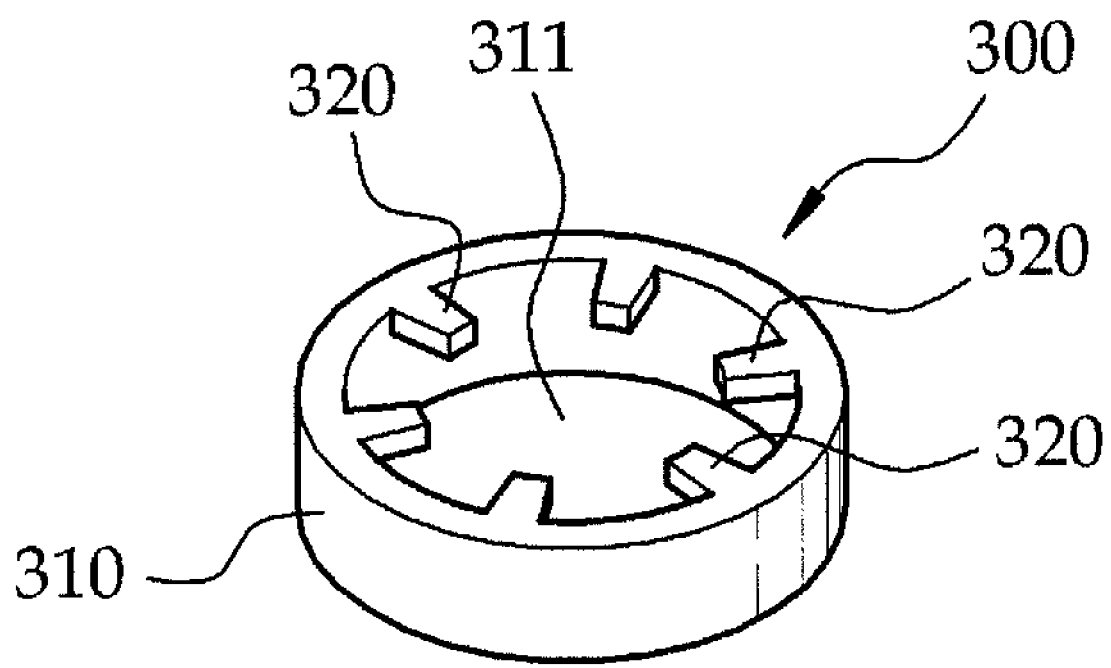
FIG. 10 is a perspective view of a protection jig having another shape that can be used in FIGS. 6 through 9.

For example, the protection jig 230 of FIG. 7 is used but a protection jig 300 having a shape as illustrated in FIG. 10 may be used. The protection jig 300 of FIG. 10 is disposed in such a way that a plurality of fixed protrusions 320 formed in internal sides of a combination hole 311 of a body portion 310 are separated from one another in a circumferential direction of the combination hole 311. The fixed protrusions 320 of the protection jig 300 are inserted in the fixed groove 212 of the fixture 200 and are fixed therein, like the fixed protrusions 233 of the protection jig 230 of FIG. 7.

In addition, the fixed protrusions 233 of the protection jig 230 of FIG. 7 and the fixed protrusions 320 of the protection jig 300 of FIG. 10 are respectively located adjacent to an upper side of the body portion 231 of the protection jig 230 of FIG. 7 and an upper side of the body portion 310 of the protection jig 300 of FIG. 10. However, in some cases, the fixed protrusions 233 of FIG. 7 and the fixed protrusions 320 of FIG. 10 may be respectively located adjacent to a lower side of the body portion 231 of the protection jig 230 of FIG. 7 and a lower side of the body portion 310 of the protection jig 300 of FIG. 10 or may be disposed at middle inner walls of the body portion 231 of the protection jig 230 of FIG. 7 and middle inner walls of the body portion 310 of the protection jig 300 of FIG. 10.

As described above, in a method of manufacturing a fixture of a dental implant according to the present invention, the fixture of the dental implant in which the performance of osseointegration is excellent and spread of inflammation can be reduced, can be easily manufactured.

Furthermore, in the fixture of the dental implant according to the present invention, the performance of osseointegration is excellent and spread of inflammation can be reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of manufacturing a fixture of a dental implant, the method comprising:
    cutting the fixture of the dental implant to form a male screw portion of the fixture;
    forming a fixed groove in the male screw portion of the fixture to surround a portion of the male screw portion in a circumferential direction of the male screw portion, wherein a protection jig comprising a body portion having a combination hole inserted and fixed in the male screw portion of the fixture; and at least one fixed protrusion formed in an internal side of the combination hole so as to be inserted in the fixed groove of the fixture and fixed therein;
    performing jig fixing in such a way that the protection jig is inserted in a ring-shaped male screw portion to surround a portion of the male screw portion of the fixture in a circumferential direction of the protection jig;
    performing surface processing on the male screw portion of the fixture to increase a surface roughness; and
    performing jig removal in such a way that the protection jig fixed on the male screw portion is removed from the male screw portion of the fixture.

2. The method of claim 1, wherein the protection jig is formed of polymer having elasticity.

3. The method of claim 1, wherein a female screw portion is formed at an inner diameter of the protection jig to be engaged with the male screw portion.

4. The method of claim 1, wherein the performing of surface processing is performed using sandblasting.

5. The method of claim 1, wherein the performing of surface processing is performed using anodization.

6. The method of claim 1, wherein the fixed protrusion of the protection jig is ring-shaped.

7. The method of claim 1, wherein a plurality of fixed protrusions of the protection jig are disposed in such a way that the plurality of fixed protrusions of the protection jig are separated from one another in a circumferential direction of the combination hole.

* * * * *